(12) United States Patent
Kimbahune et al.

(10) Patent No.: US 9,953,415 B2
(45) Date of Patent: Apr. 24, 2018

(54) **SYSTEM AND METHOD FOR QUANTIFICATION OF *ESCHERICHIA COLI* BACTERIA IN WATER**

(71) Applicant: Tata Consultancy Services Limited, Mumbai (IN)

(72) Inventors: Sanjay Madhukar Kimbahune, Thane (IN); Sunil Kumar Kopparapu, Thane (IN); Syed Mohammad Ghouse, Thane (IN); Kishore Padmanabhan, Siruseri (IN)

(73) Assignee: Tata Consultancy Services Limited, Mumbai (IN)

( * ) Notice: Subject to any disclaimer, the term of this patent is extended or adjusted under 35 U.S.C. 154(b) by 199 days.

(21) Appl. No.: 14/956,954

(22) Filed: Dec. 2, 2015

(65) Prior Publication Data

US 2016/0163046 A1    Jun. 9, 2016

(30) Foreign Application Priority Data

Dec. 3, 2014   (IN) .......................... 3880/MUM/2014

(51) Int. Cl.
*G06K 9/00* (2006.01)
*G06T 7/00* (2017.01)
(Continued)

(52) U.S. Cl.
CPC .............. *G06T 7/0012* (2013.01); *C12Q 1/10* (2013.01); *G06T 7/90* (2017.01); *G06T 2207/10024* (2013.01); *G06T 2207/30024* (2013.01)

(58) Field of Classification Search
CPC .................... G06T 7/0012; G06T 7/90; G06T 2207/30024; C12R 1/19
(Continued)

(56) References Cited

U.S. PATENT DOCUMENTS 7,116,820 B2    10/2006  Luo et al.
7,122,338 B2 *  10/2006  Crouteau .............. B01L 3/5085
                                                      435/287.9

(Continued)

OTHER PUBLICATIONS

Gunda, N.S.K. et al, (Aug. 2014). Mobile Water Kit (MWK): a smartphone compatible low-cost water monitoring system for rapid detection of total coliform and *E. coli*, Analytical Methods, vol. 6, No. 16, pp. 6236-6246.

(Continued)

*Primary Examiner* — Van D Huynh
(74) *Attorney, Agent, or Firm* — Finnegan, Henderson, Farabow, Garrett & Dunner LLP

(57) ABSTRACT

A system and method for quantification of *Escherichia Coli* bacteria in water is disclosed. In an embodiment, a region of interest (ROI) is obtained from an image of the water. For example, the ROI includes a plurality of pixels in the image of water contaminated with *Escherichia Coli* bacteria. Further, a plurality of red pixels are identified from the ROI based on a value of the plurality of pixels in the ROI and a threshold value. Furthermore, total redness of the plurality of red pixels in the ROI is calculated based on intensity of plurality of red pixels. In addition, a redness factor indicative of a degree of redness of the ROI is computed based on the calculated total redness. Quantification of the *Escherichia Coli* bacteria is then estimated based on the computed redness factor.

13 Claims, 8 Drawing Sheets

(51) Int. Cl.
*C12Q 1/10* (2006.01)
*G06T 7/90* (2017.01)

(58) Field of Classification Search
USPC .......................................................... 382/103
See application file for complete search history.

(56) References Cited

U.S. PATENT DOCUMENTS

| | | | |
|---|---|---|---|
| 8,472,661 B2 | 6/2013 | Bick | |
| 2002/0136450 A1* | 9/2002 | Chen | G06K 9/0061 |
| | | | 382/165 |
| 2006/0063225 A1 | 3/2006 | Caulfield et al. | |
| 2008/0153125 A1* | 6/2008 | Buttry | C12Q 1/04 |
| | | | 435/30 |
| 2010/0007505 A1* | 1/2010 | Adams | G01N 21/53 |
| | | | 340/627 |
| 2014/0242612 A1 | 8/2014 | Wang et al. | |
| 2015/0247190 A1 | 9/2015 | Ismagilov et al. | |
| 2016/0355871 A1* | 12/2016 | Want | C12Q 1/689 |
| 2017/0121688 A1* | 5/2017 | Gil | C12N 7/00 |

OTHER PUBLICATIONS

Koydemir, H.C. et al. (Mar. 2015). "Rapid imaging, detection and quantification of *Giardia lamblia* cysts using mobile-phone based fluorescent microscopy and machines learning," *Lab Chip*, vol. 15, No. 5, pp. 1284-1293.

* cited by examiner

| SR. NO. | THRESHOLD VALUES (β) | OBSERVATIONS |
|---|---|---|
| 1 | 0 TO 0.5 | ALL RED AND NON-RED PIXELS ARE EXTRACTED |
| 2 | 0.5 TO 0.8 | ALL RED AND FEW NON-RED PIXELS ARE EXTRACTED |
| 3 | 0.8 TO 1.2 | ALL RED PIXELS WITH HIGH INTENSITY AND LOW INTENSITY ARE EXTRACTED |
| 4 | 1.2 TO 2.6 | RED PIXELS WITH MEDIUM AND HIGH INTENSITY ARE EXTRACTED |
| 5 | 2.6 TO 4.8 | ONLY HIGH INTENSITY RED PIXELS ARE EXTRACTED |
| 6 | >4.9 | FEWER NUMBER OF RED PIXELS ARE EXTRACTED |

| SR. NO | IMAGE NAME | TOTAL REDNESS | AREA OF THE ROI | NO. OF SELECTED RED PIXELS | REDNESS FACTOR | RF*10^6 | CFU |
|---|---|---|---|---|---|---|---|
| 1 | IMG1 | 0 | 922780 | 0 | 0.1 | 0 | NO |
| 2 | IMG2 | 112.6676 | 913817 | 89 | 1.39E-06 | 1.3853 | NO |
| 3 | IMG3 | 19.7782 | 861254 | 16 | 1.44E-06 | 1.4353 | NO |
| 4 | IMG4 | 21712.97 | 874846 | 16335 | 1.52E-06 | 1.5194 | LOW |
| 5 | IMG5 | 118550.7 | 882439 | 84580 | 1.59E-06 | 1.5884 | LOW |
| 6 | IMG6 | 91983.8 | 877804 | 64114 | 1.63E-06 | 1.6344 | LOW |
| 7 | IMG7 | 122490.6 | 845645 | 86008 | 1.68E-06 | 1.6841 | MEDIUM |
| 8 | IMG8 | 127180.7 | 845748 | 86371 | 1.74E-06 | 1.7411 | MEDIUM |
| 9 | IMG9 | 109657.6 | 804358 | 77160 | 1.77E-06 | 1.7668 | MEDIUM |
| 10 | IMG10 | 101896.2 | 829943 | 68895 | 1.78E-06 | 1.7821 | MEDIUM |
| 11 | IMG11 | 190220.6 | 855826 | 124362 | 1.79E-06 | 1.7872 | HIGH |
| 12 | IMG12 | 168582.9 | 847742 | 103175 | 1.93E-06 | 1.9274 | HIGH |
| 13 | IMG13 | 148385.5 | 849289 | 90561 | 1.93E-06 | 1.9293 | HIGH |
| 14 | IMG14 | 77770.15 | 860933 | 45940 | 1.97E-06 | 1.9663 | HIGH |
| 15 | IMG15 | 413921.4 | 926849 | 213070 | 2.1E-06 | 2.096 | HIGH |
| 16 | IMG16 | 808637.5 | 904841 | 415302 | 2.15E-06 | 2.1519 | HIGH |

| SR. NO | CFU | RF*10^6 RANGE |
|---|---|---|
| 1 | NO | 0-1.4352 |
| 2 | LOW | 1.5194 – 1.6344 |
| 3 | MEDIUM | 1.6841 – 1.7821 |
| 4 | HIGH | 1.7872 – 2.1519 |

SYSTEM AND METHOD FOR QUANTIFICATION OF ESCHERICHIA COLI BACTERIA IN WATER

PRIORITY CLAIM

This U.S. patent application claims priority 35 U.S.C. § 119 to: Indian provisional specification no. 3880/MUM/2014 filed on Dec. 3, 2014. The entire contents of the aforementioned application are incorporated herein by reference.

TECHNICAL FIELD

The embodiments herein generally relate to water contaminated with *Escherichia Coli* bacteria, and more particularly, for quantification of *Escherichia Coli* bacteria in water.

BACKGROUND

Public health protection requires safe drinking water, which is free of pathogenic bacteria. Typically, water-related diseases are caused by consumption of water that is contaminated with human or animal fecal material. Pathogens such as *Escherichia Coli* (*E. coli*) are generally present in very low concentrations in environmental waters within a diversified microflora. The presence of *E. coli* has long been established as the most reliable microbiological indication of water quality and presence of fecal contamination in water. Detection and quantification of bacteria is important for monitoring the sanitation of water. Culture methods are routinely used for detection and quantification of the presence of *E. coli*.

Existing culture-based methods perform a selective culture step followed by biochemical or genetic confirmation of presumptive *E. coli* colonies or cultures. Typical culture-based methods require advanced techniques, laboratory environment or (incubators) and trained professional with specialized skills to use the techniques. Thus, culture-based methods are tedious, cost-intensive and time consuming.

SUMMARY

The following presents a simplified summary of some embodiments of the disclosure in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented below. In view of the foregoing, an embodiment herein provides water contaminated with *Escherichia Coli* bacteria, and more particularly, for quantification of *Escherichia Coli* bacteria in water.

In one aspect, a method for quantification of *Escherichia Coli* bacteria in water is disclosed. In an embodiment, a region of interest (ROI) is obtained from an image of a syringe filter upon transferring water contaminated with *Escherichia Coli* bacteria. The ROI includes a plurality of pixels in the image of the syringe filter upon transferring water contaminated with *Escherichia Coli* bacteria. Further, a plurality of red pixels are extracted from the ROI based on a value of the plurality of pixels in the ROI and a threshold value. Furthermore, total redness of the plurality of red pixels in the ROI is calculated based on intensity of plurality of red pixels. In addition, a redness factor indicative of a degree of redness of the ROI is computed based on the calculated total redness. Quantification of the *Escherichia Coli* bacteria is then quantified based on the computed redness factor.

In another aspect, a system for quantification of *Escherichia Coli* bacteria in water is disclosed. In an embodiment, the system includes one or more processors and a memory communicatively coupled to the one or more processors. The memory includes a quantification module. In this embodiment, the quantification module obtains a ROI from an image of a syringe filter upon transferring water contaminated with *Escherichia Coli* bacteria. The ROI includes a plurality of pixels in the image of the syringe filter upon transferring water contaminated with *Escherichia Coli* bacteria. Further, the quantification module extracts a plurality of red pixels from the ROI based on a value of the plurality of pixels in the ROI and a threshold value. Furthermore, the quantification module calculates a total redness of the plurality of red pixels in the ROI based on intensity of plurality of red pixels. In addition, the quantification module determines a redness factor indicative of a degree of redness of the ROI based on the calculated total redness. Also, the quantification module estimates quantification of the *Escherichia Coli* bacteria based on the computed redness factor.

These and other aspects of the embodiments herein will be better appreciated and understood when considered in conjunction with the following description and the accompanying drawings. It should be understood, however, that the following description, while indicating preferred embodiments and numerous specific details thereof, are given by way of illustration. The summary is not intended to identify essential features of the claimed subject matter nor is it intended for use in determining or limiting the scope of the claimed subject matter. Changes and modifications may be made within the scope of the embodiments herein.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION

Figure 1:
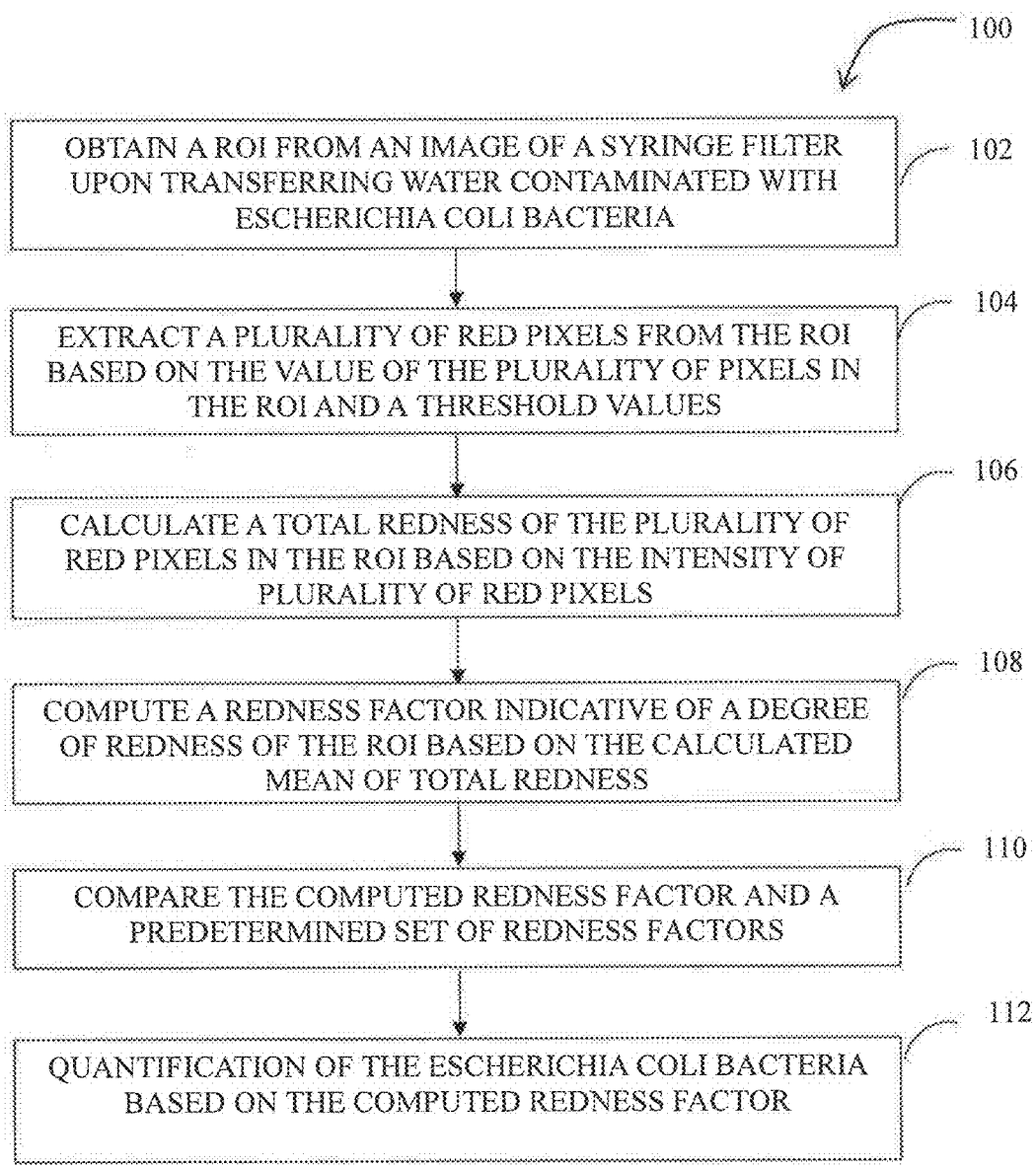
FIG. 1 is a flow diagram illustrating a method for quantification of *Escherichia Coli* bacteria in water, in accordance with some embodiments of the present disclosure.

The embodiments herein and the various features and advantageous details thereof are explained more fully with reference to the non-limiting embodiments that are illustrated in the accompanying drawings and detailed in the following description. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

Referring now to the drawings, and more particularly to FIG. 1 through 8, where similar reference characters denote corresponding features consistently throughout the figures, there are shown preferred embodiments and these embodiments are described in the context of the following exemplary system and/or method.

FIG. 1 is a flow diagram 100 illustrating a method for quantification of *Escherichia Coli* bacteria in water, according to an embodiment of the present disclosure. At block 102, a Region of Interest (ROI) is obtained from an image of the syringe filter upon transferring water contaminated with *Escherichia Coli* bacteria. For example, the ROI includes a plurality of pixels in the image of the syringe filter upon transferring water contaminated with *Escherichia Coli* bacteria.

In an exemplary embodiment, water sample is collected and transferred to a syringe filter. Further, *Escherichia Coli* bacteria in the water changes color of the syringe filter to red color. In general, the syringe filter is surrounded by a blue ring represents the contamination and provide protection to the ROI. Generally, the ROI is a region inside the blue ring. In this example, a degree of contamination is directly proportional to an intensity and spread of the red color in the syringe filter. Further, an image of the syringe filter is obtained using an image capturing device (e.g. a camera and the like). For example, the image includes three components, such as red, green and blue (RGB) components. Furthermore, red (R), green (G) and blue (B) band images are extracted from the captured image of the syringe filter by separating the RGB components, respectively. Each of the plurality of pixels includes a red component value, a green component value and/or a blue component value.

In addition, the blue ring surrounding the syringe filter is detected. For example, the blue ring includes blue colored pixels which have lower values of red and green bands and higher values of a blue band. In an example implementation to detect the blue ring, threshold ranges are defined to all three RGB bands. For example, an Otsu's method is used to compute the threshold ranges (an inbuilt matlab function (graythresh) is used to compute the threshold ranges). The threshold ranges are used to binarize the grey images. In an example, the threshold range defined for the red band is 0 to graythresh (red_band)*255. The threshold range defined for the green band is 0 to graythresh (green_band)*255. The threshold range defined for the blue band is graythresh (blue_band)*255 to 255. In some embodiments, Otsu's methodology is employed to compute clustering-based image thresholding. The above methodology makes an assumption that the image contains two classes of pixels following bi-modal histogram and then computes an optimum threshold separating the two classes so that their combined spread is minimal.

Further in this example implementation, masking is applied on each of the RGB band images with the associated threshold ranges. Upon masking, the portion which is blue in the captured image appears to be binary 1 in all the three masked images of different bands. Binary mask allows specifying transparent areas when a given image is intended to be placed over a background. In the images, the black pixels have the all-zero values and white pixels have the all-one values.

Furthermore, a logical AND operation is performed on the three masked images namely a red mask, a green mask and a blue mask to form a blue ring image and to detect the blue ring. In this scenario, position the images on the screen over the background, and masks the screen pixel's bits with the image mask at the desired coordinates namely the red mask, the green mask and the blue mask using the logical AND operation to detect the blue ring. Also, standard image processing techniques, such as bwareopen, imclose and bwconn comp are used to remove the portion of the other blue rings, small marks, noise data etc. and to smoothen the borders in the blue ring image.

In addition, ROI indices are extracted from the blue ring image using a below method:
1. Traverse a row and perform the following:
   a. If no white pixel (binary 1) is found, make all the row white (binary 1).
   b. If any white pixel is found then perform the following:
      (i) Stop and make the row white till this point.
      (ii) Start traversing the same row from the other end till the white pixel is found and make the row white till this point.
2. Repeat the step 1 for all the rows in the blue ring image
3. Finally complement the resultant image.
4. Save the indices of the white pixels (e.g., the ROI indices).

At the extracted ROI index locations, concatenate all the three color bands (RGB) to get the color image of the ROI.

At block 104, a plurality of red pixels are extracted from the ROI based on a value of the plurality of pixels in the ROI and threshold values. In an example, red pixels are extracted from ROI using a below equation (1):

$$R_{ij} > (G_{ij} B_{ij})^{1/2} \quad (1)$$

Applying logarithm on both sides, $$\log(R_{ij}) > \frac{\log(G_{ij}) + \log(B_{ij})}{2} \quad (2)$$

When the RGB component value of the pixel is 0, to overcome the log (0) error, add 1 inside the logarithm term as shown in below equation:

$$2*\log(R_{ij}+1) > \log(G_{ij}+1) + \log(B_{ij}+1) \quad (3)$$

$$2*\log(R_{ij}+1) - \log(G_{ij}+1) - \log(B_{ij}+1) > 0 \quad (4)$$

Almost all the pixels in the ROI satisfy the above condition. So a threshold value ($\beta$) is used to extract only the red pixels.

In an example implementation, the threshold value ($\beta$) is determined using a method by initializing $\beta$ value is equal to 0 and extracting the red pixels from the ROI. Further, observe if any non-red color pixels are extracted. Further, if $\beta$ value is equal to 11.09 end the process, else increase the β value to 0.1 and continue the process. Upon determining the β value, the plurality of red pixels are extracted from the ROI when a difference between two times red component value of a pixel and a sum of a green component value of the pixel and a blue component value of the pixel is greater than the threshold value using a below example equation (5).

$$2*\log(R_{ij}+1)-\log(G_{ij}+1)-\log(B_{ij}+1)>\beta \quad (5)$$

where, $R_{ij}$ is the red component value of the pixel at the location i,j, $G_{ij}$ is the green component value of the pixel at the location i,j, $B_{ij}$ is the blue component value of the pixel at the location i,j, β is a threshold values, ij are the variables and Log is equal logarithm with respect to the base e.

Figure 2:
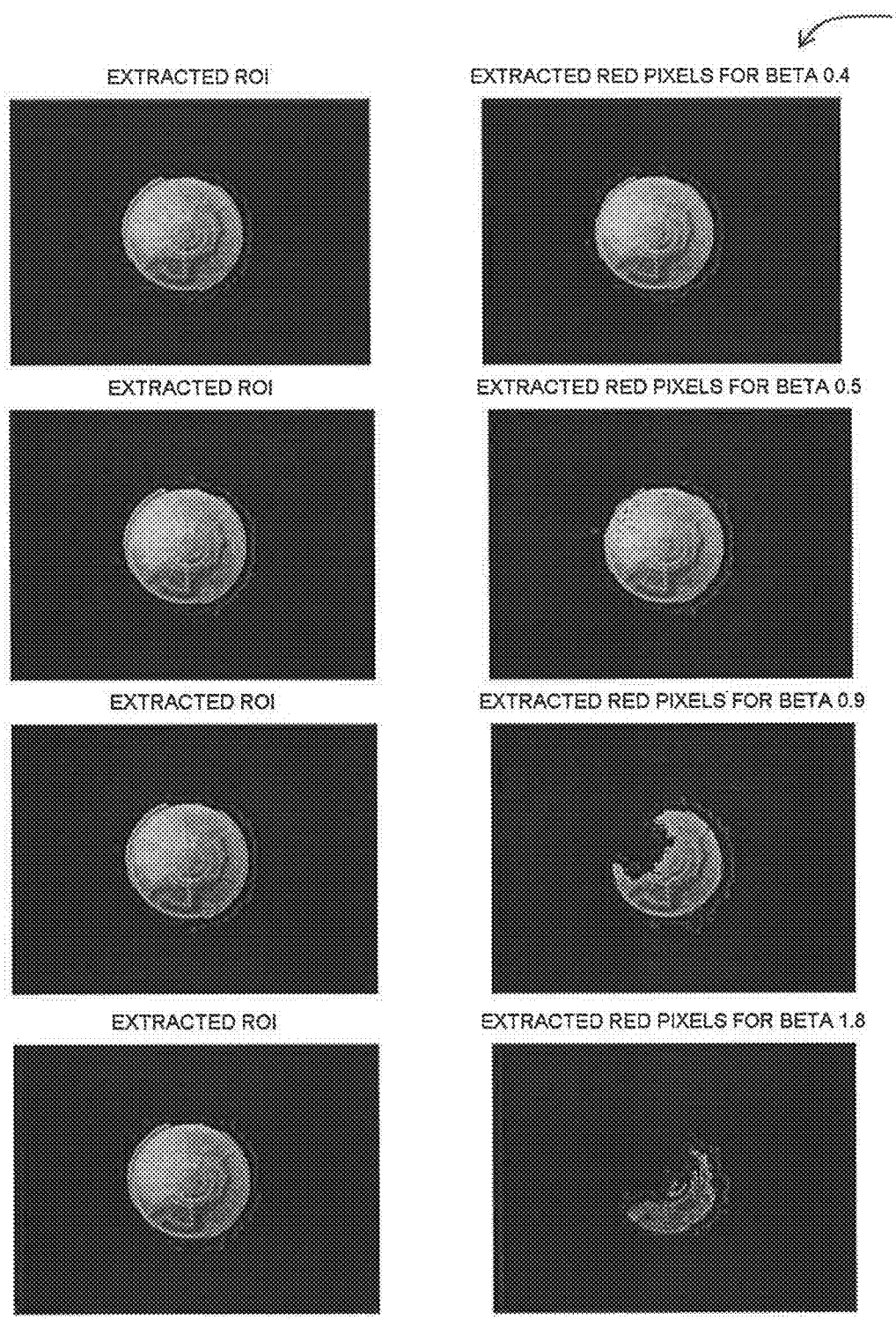
FIG. 2 illustrates exemplary images of red pixels are extracted from the ROI with different threshold values, in accordance with some embodiments of the present disclosure.
Figure 3:
FIG. 3 is a table illustrating observations over several ROI images on extracting on red pixels while determining threshold value, in accordance with some embodiments of the present disclosure.
Figure 4:
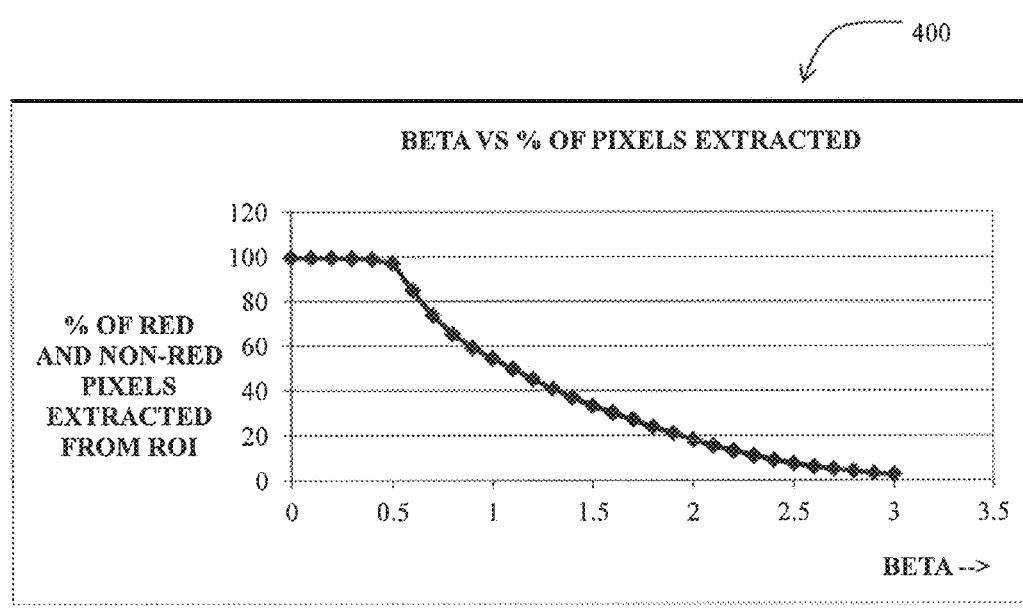
FIG. 4 illustrates a graph between all pixels extracted from a ROI with threshold values, in accordance with some embodiments of the present disclosure.

An exemplary image of 200 explains the red pixels extracted from the ROI with different threshold values are shown in FIG. 2. The images of the extracted red pixels from the ROI are obtained with different threshold (β) values ranges from (0.4, 0.5, 0.9, 1.8). Further, a table 300 of FIG. 3 illustrates the observations over several ROI images on extracting on red pixels while determining threshold value. Further, in an example the 1 ranging from 0.8 to 1.2 is considered as the suitable range of thresholds to extract all the red pixels from the ROI. In addition, FIG. 4 explains a graph 400 between all pixels extracted from ROI with the threshold values. Further, for this experimentation a value of 1.18 is considered as the threshold value to extract the red pixels from the ROI.

In an embodiment, extracted red pixels from the ROI have different color intensities. At block 106, a total redness of the plurality of red pixels in the ROI is calculated based on the intensity of plurality of red pixels. In an embodiment, redness of each of the plurality of red pixels is determined based on the intensity of plurality of red pixels. For example, the redness of each of the plurality of red pixels is a difference between the two times of a red component value of a red pixel and a sum of a green component value of the red pixel and a blue component value of the red pixel as shown in a below equation (6).

$$f(R,G,B)=2*\log(R_{ij}+1)-\log(G_{ij}+1)-\log(B_{ij}+1) \quad (6)$$

where, $R_{ij}$ is the red component value of the red pixel at the location i,j, $G_{ij}$ is the green component value of the red pixel at the location i,j, $B_{ij}$ is the blue component value of the red pixel at the location i,j, i,j are the variables and Log is a logarithm with respect to the base e.

Furthermore, the total redness of the plurality of red pixels is calculated by summation of the redness of each of the plurality of red pixels.

At block 108, a redness factor (RF) indicative of a degree of redness of the ROI is computed based on the calculated total redness. In an example implementation, a mean value of the total redness of the ROI is calculated based on the ratio of the total redness of the ROI to the number of plurality of the red pixels in the ROI. For example, the mean value of the total redness of the ROI is calculated using a below equation (7):

$$\text{Mean of Total redness} = \frac{\sum_{ext.\ red\ RGB} f(R,G,B)}{\text{No. of red pixels in ROI}} \quad (7)$$

Where $\Sigma_{ext.\ red\ RGB} f(R, G, B)$ is the total redness of the image of the ROI.

Further in this implementation, the RF indicative of the degree of redness of the ROI is then computed based on the calculated mean value of the total redness.

$$\text{Redness factor}(RF) = \frac{\sum_{ext.\ red\ RGB} f(R,G,B)}{\text{No. of red pixels in ROI} * \text{Area of the ROI}} \quad (8)$$

Figure 5:
FIG. 5 is table illustrating exemplary dataset used in determining redness factor with threshold value, in accordance with some embodiments of the present disclosure.
Figure 6:
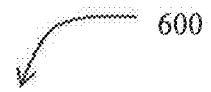
FIG. 6 is a table illustrating a range of redness factor values for the CFU classes, shown in FIG. 5, in accordance with some embodiments of the present disclosure.

In one example, a sample dataset used in determining RF along with the CFU categories is shown in a table 500 of FIG. 5. At block 110, computed redness factor is compared with a set of predetermined redness factors shown in a table 600 of FIG. 6. In an embodiment, the redness factor is computed for all the images with known *E. coli* concentration which is measured in terms of CFU/ml (Colony Forming Unit) as shown below.

1. No (0 CFU)
2. Low (1-1000 CFU)
3. Medium (1001-20000 CFU)
4. High (20001-200000000 CFU)

Figure 7:
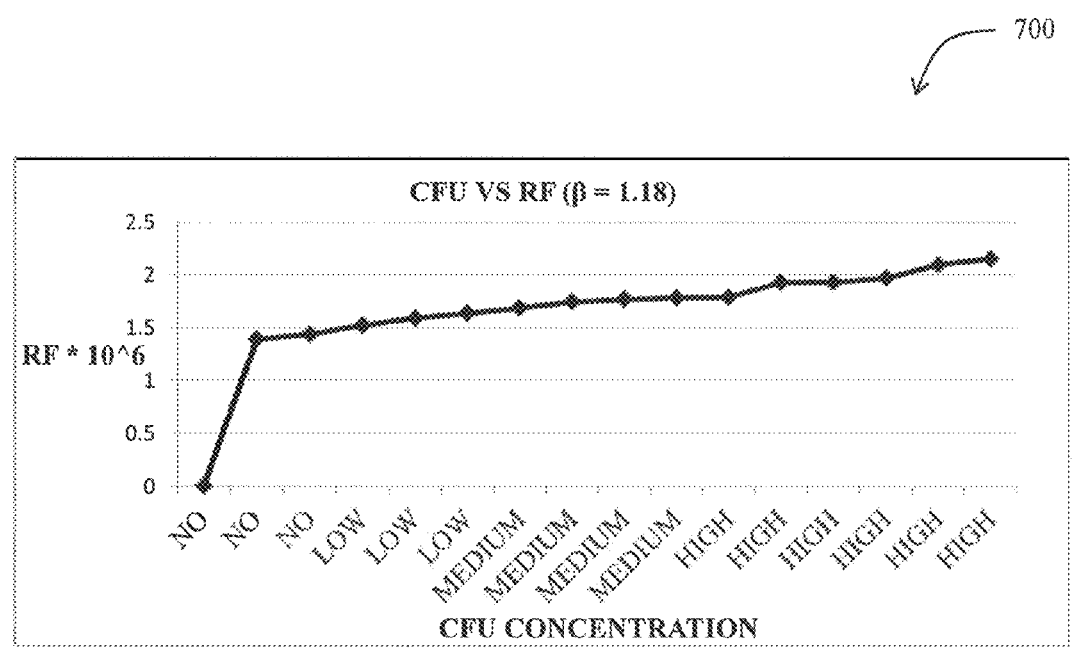
FIG. 7 illustrates a graph between the range of redness factor values and the CFU classes, in accordance with some embodiments of the present disclosure.

In an example, 10^6 multiplier is applied on RF factor as the redness value is very small. Further, the range of RF values for the CFU categories is shown in the table 600 of FIG. 6. FIG. 7 indicates the graph 700 between the CFU categories and redness factor multiplied by 10^6. The graph 700 shows that all the CFU categories can be classified based on RF value.

At block 112, the *Escherichia Coli* bacteria in the water is quantified based on the comparison at block 110. Particularly, the computed redness factor is used to quantify the *E. coli* bacteria contamination with the respective CFU category.

The order in which the method(s) are described is not intended to be construed as a limitation, and any number of the described method blocks can be combined in any order to implement the method 100, or an alternative method. Additionally, individual blocks may be deleted from the methods without departing from the spirit and scope of the subject matter described herein. Furthermore, the method 100 can be implemented in any suitable hardware, software, firmware, or combination thereof.

In an implementation, one or more of the method(s) described herein may be implemented at least in part as instructions embodied in non-transitory computer-readable storage medium and executable by one or more computing devices. In general, a processor (for example a microprocessor) receives instructions, from a non-transitory computer-readable medium, for example, a memory, and executes those instructions, thereby performing one or more method(s), including one or more of the method(s) described herein. Such instructions may be stored and/or transmitted using any of a variety of known computer-readable media.

Figure 8:
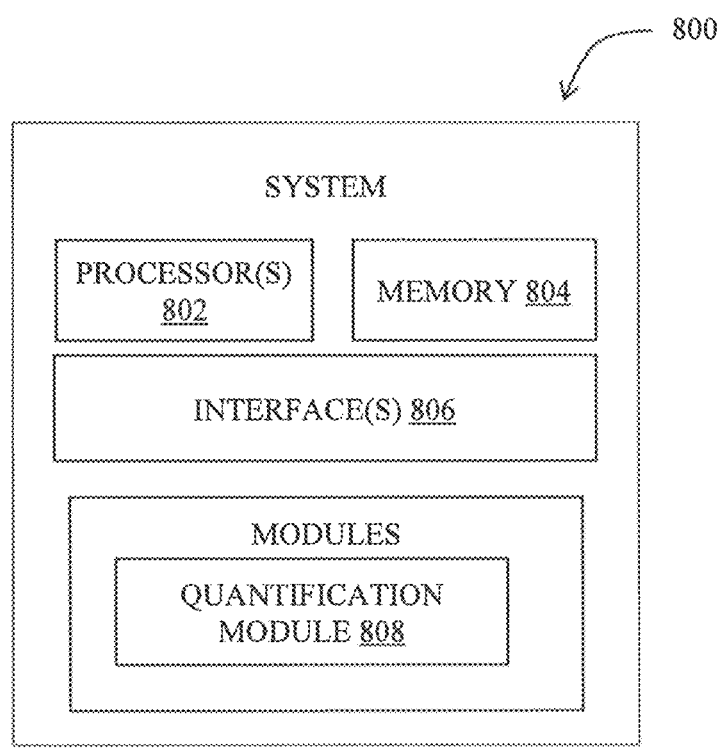
FIG. 8 illustrates a system for quantification of *Escherichia Coli* bacteria in water, in accordance with some embodiments of the present disclosure.

FIG. 8 illustrates a system 800 for quantification of *Escherichia Coli* bacteria in water, according to an embodiment of the present disclosure. Although the present subject matter is explained considering that the system is implemented as a server, it may be understood that the system may also be implemented as a variety of computing systems, such as a laptop computer, a desktop computer, a notebook, a workstation, a mainframe computer, a server, a network server, a tablet, a mobile phone, a robot and the like. In one implementation, the system may be implemented in a cloudbased environment. It will be understood that the system may be accessed by multiple users through one or more user devices.

As shown in FIG. 8, the system 800 includes one or more processor(s) 802 and a memory 804 communicatively coupled to each other. The system 800 also includes interface(s) 806. Further, the memory 804 includes modules, such as a quantification module 808. Although FIG. 8 shows example components of the system 800, in other implementations, the system 800 may contain fewer components, additional components, different components, or differently arranged components than depicted in FIG. 8.

The processor(s) 802 and the memory 804 may be communicatively coupled by a system bus. The processor(s) 802 may include circuitry implementing, among others, audio and logic functions associated with the communication. The processor(s) 802 may include, among other things, a clock, an arithmetic logic unit (ALU) and logic gates configured to support operation of the processor(s) 802. The processor(s) 802 can be a single processing unit or a number of units, all of which include multiple computing units. The processor(s) 802 may be implemented as one or more microprocessors, microcomputers, microcontrollers, digital signal processors, central processing units, state machines, logic circuitries, and/or any devices that manipulate signals based on operational instructions. Among other capabilities, the processor(s) 802 is configured to fetch and execute computer-readable instructions and data stored in the memory 804.

The functions of the various elements shown in the figure, including any functional blocks labeled as "processor(s)", may be provided through the use of dedicated hardware as well as hardware capable of executing software in association with appropriate software. When provided by a processor, the functions may be provided by a single dedicated processor, by a single shared processor, or by a plurality of individual processors, some of which may be shared. Moreover, explicit use of the term "processor" should not be construed to refer exclusively to hardware capable of executing software, and may implicitly include, without limitation, digital signal processor (DSP) hardware, network processor, application specific integrated circuit (ASIC), field programmable gate array (FPGA), read only memory (ROM) for storing software, random access memory (RAM), and non-volatile storage. Other hardware, conventional, and/or custom, may also be included.

The interface(s) 806 may include a variety of software and hardware interfaces, for example, interfaces for peripheral device(s), such as a keyboard, a mouse, an external memory, and a printer. The interface(s) 806 can facilitate multiple communications within a wide variety of networks and protocol types, including wired networks, for example, local area network (LAN), cable, etc., and wireless networks, such as Wireless LAN (WLAN), cellular, or satellite. For the purpose, the interface(s) 806 may include one or more ports for connecting the system 800 to other sources or image capturing devices.

In one implementation, the system 800 may connect to the other sources or image capturing devices via a network, such as a wireless network, a wired network or a combination thereof. The network can be implemented as one of the different types of networks, such as intranet, local area network (LAN), wide area network (WAN), the internet, and the like. The network may either be a dedicated network or a shared network. The shared network represents an association of the different types of networks that use a variety of protocols, for example, Hypertext Transfer Protocol (HTTP), Transmission Control Protocol/Internet Protocol (TCP/IP), Wireless Application Protocol (WAP), and the like, to communicate with one another. Further, the network may include a variety of network devices, including routers, bridges, servers, computing devices, storage devices, and the like.

The memory 804 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. The memory 804, may store any number of pieces of information, and data, used by the system 800 to implement the functions of the system 800. The memory 804 may be configured to store information, data, applications, instructions or the like for enabling the system 800 to carry out various functions in accordance with various example embodiments. Additionally or alternatively, the memory 804 may be configured to store instructions which when executed by the processor 802 causes the system 800 to behave in a manner as described in various embodiments. The memory 804 includes the quantification module 808 and other modules. The module 808 includes routines, programs, objects, components, data structures, etc., which perform particular tasks or implement particular abstract data types. The other modules may include programs or coded instructions that supplement applications and functions of the system 800.

In an embodiment, the quantification module 808 obtains a ROI from an image of the syringe filter upon transferring water contaminated with *Escherichia Coli* bacteria. For example, the ROI includes a plurality of pixels in the image of the syringe filter upon transferring water contaminated with *Escherichia Coli* bacteria. Further, the quantification module 808 identifies a plurality of red pixels from the ROI based on a value of the plurality of pixels in the ROI and a threshold value. Furthermore, the quantification module 808 calculates a total redness of the plurality of red pixels in the ROI based on intensity of plurality of red pixels. In addition, the quantification module 808 determines a redness factor indicative of a degree of redness of the ROI based on the calculated total redness. Also, the quantification module 808 estimates quantification of the *Escherichia Coli* bacteria based on the computed redness factor. This is explained in more detail with reference to FIG. 1.

It is, however to be understood that the scope of the protection is extended to such a program and in addition to a computer-readable means having a message therein; such computer-readable storage means contain program-code means for implementation of one or more steps of the method, when the program runs on a server or mobile device or any suitable programmable device.

The preceding description has been presented with reference to various embodiments. Persons having ordinary skill in the art and technology to which this application pertains appreciate that alterations and changes in the described structures and methods of operation can be practiced without meaningfully departing from the principle, spirit and scope.

What is claimed is:

1. A method for quantification of *Escherichia Coli* bacteria in water, the method comprising processor implemented steps of:

obtaining a region of interest (ROI) from an image of a syringe filter upon transferring water contaminated with *Escherichia Coli* bacteria, wherein the ROI comprises a plurality of pixels in the image of the syringe filter, wherein the plurality of pixels comprise white pixels and wherein the white pixels are determined based on a binary value of pixels in a plurality of rows of the image;

extracting a plurality of red pixels from the ROI based on a value of the plurality of pixels in the ROI and a threshold value, wherein the plurality of red pixels are extracted from the plurality of pixels in the ROI when a difference between two times of red component value of a pixel and a sum of a green component value of the pixel and a blue component value of the pixel is greater than the threshold value;

calculating a total redness of the plurality of red pixels in the ROI based on intensity of the plurality of red pixels;

computing a redness factor indicative of a degree of redness of the ROI based on the calculated total redness; and estimating the quantification of the *Escherichia Coli* bacteria based on the computed redness factor.

2. The method of claim 1, wherein calculating the total redness of the plurality of red pixels in the ROI comprises processor implemented steps of:

determining redness of each of the plurality of red pixels based on the intensity of associated one of the plurality of red pixels; and calculating total redness of the plurality of red pixels by summation of the determined redness of each of the plurality of red pixels.

3. The method of claim 2, wherein the redness of each of the plurality of red pixels is a difference between two times of red component value of a red pixel and a sum of green component value of the red pixel and blue component value of the red pixel.

4. The method of claim 1, wherein computing the redness factor indicative of the degree of redness of the ROI comprises processor implemented steps of:

calculating a mean value of the total redness of the ROI based on a ratio of the total redness of the ROI; and computing the RF indicative of the degree of redness of the ROI based on the calculated mean value of the total redness.

5. The method of claim 4, wherein calculating the mean value of the total redness of the ROI based on the ratio of the total redness of the ROI to the number of plurality of the red pixels in the ROI.

6. The method of claim 1, wherein quantification of the *Escherichia Coli* bacteria based on the computed redness factor comprises processor implemented steps of:

comparing the computed redness factor and a set of predetermined redness factors; and quantification of the *Escherichia Coli* bacteria in the water based on the comparison.

7. A system for quantification of *Escherichia Coli* bacteria in water, the system comprising:

at least one processor; and a memory communicatively coupled to the at least one processor, wherein the at least one processor is capable of executing programmed instructions stored in the memory to:

obtain a region of interest (ROI) from an image of a syringe filter upon transferring water contaminated with *Escherichia Coli* bacteria, wherein the ROI comprises a plurality of pixels in an image of the syringe filter, wherein the plurality of pixels comprise white pixels and wherein the white pixels are determined based on a binary value of pixels in a plurality of rows of the image;

extract a plurality of red pixels from the ROI based on value of the plurality of pixels in the ROI and a threshold value, wherein the plurality of red pixels are extracted from the plurality of pixels in the ROI when a difference between two times of red component value of a pixel and a sum of a green component value of the pixel and a blue component value of the pixel is greater than the threshold value;

calculate a total redness of the plurality of red pixels in the ROI based on the intensity of the plurality of red pixels;

compute a redness factor indicative of a degree of redness of the ROI based on the calculated total redness; and estimate the quantification of the *Escherichia Coli* bacteria based on the computed redness factor.

8. The system of claim 7, wherein the at least one processor is capable of executing programmed instructions to calculate redness of each of the plurality of red pixels based on the intensity of associated one of the plurality of red pixels and wherein the quantification module calculates total redness of the plurality of red pixels by summation of the determined redness of each of the plurality of red pixels.

9. The system of claim 7, wherein the at least one processor is capable of executing programmed instructions to determine the redness of each of the plurality of red pixels is obtained by taking the difference between twice the red component value of the pixel and the sum of green component value of the pixel and blue component value of the pixel.

10. The system of claim 7, wherein the at least one processor is capable of executing programmed instructions to calculate the mean value of the total redness of the ROI based on the ratio of the total redness of the ROI and wherein the quantification module computes the RF indicative of a degree of redness of the ROI based on the calculated mean value of the total redness.

11. The system of claim 10, wherein the at least one processor is capable of executing programmed instructions to calculate the mean value of the total redness of the ROI based on the ratio of the total redness of the ROI to the number of plurality of the red pixels in the ROI.

12. The system of claim 7, wherein the at least one processor is capable of executing programmed instructions to compare the computed RF and a predetermined set of RF and estimate the quantification of the *Escherichia Coli* bacteria in the water based on the comparison.

13. A non-transitory computer readable medium embodying a program executable in a computing device for quantification of *Escherichia Coli* bacteria in water the program comprising:

a program code for obtaining a region of interest (ROI) from an image of a syringe filter upon transferring water contaminated with *Escherichia Coli* bacteria, wherein the ROI comprises a plurality of pixels in the image of the syringe filter, wherein the plurality of pixels comprise white pixels and wherein the white pixels are determined based on a binary value of pixels in a plurality of rows of the image;

a program code for extracting a plurality of red pixels from the ROI based on a value of the plurality of pixels in the ROI and a threshold value, wherein the plurality of red pixels are extracted from the plurality of pixels in the ROI when a difference between two times of red component value of a pixel and a sum of a green component value of the pixel and a blue component value of the pixel is greater than the threshold value;

a program code for calculating a total redness of the plurality of red pixels in the ROI based on intensity of the plurality of red pixels;

a program code for computing a redness factor indicative of a degree of redness of the ROI based on the calculated total redness; and a program code for estimating the quantification of the *Escherichia Coli* bacteria based on the computed redness factor.

* * * * *